United States Patent [19]

Kleinlogel

[11] 4,086,342

[45] Apr. 25, 1978

[54] 6-(1-PIPERAZINYL)MORPHANTHRIDINE AS A SLEEP INDUCING OR PROLONGING AGENT

[75] Inventor: Horst Kleinlogel, Hinterkappelen, Switzerland

[73] Assignee: Sandoz Ltd., Basel, Switzerland

[21] Appl. No.: 770,218

[22] Filed: Feb. 18, 1977

Related U.S. Application Data

[63] Continuation-in-part of Ser. No. 653,971, Jan. 30, 1976, abandoned.

[30] Foreign Application Priority Data

Feb. 5, 1975 Switzerland .................... 1395/75

[51] Int. Cl.$^2$ ............................................. A61K 31/495
[52] U.S. Cl. ........................................................ 424/250

[58] Field of Search ................................... 424/250

[56] References Cited

U.S. PATENT DOCUMENTS 3,389,139  6/1968  Schmutz et al. ................ 260/268

OTHER PUBLICATIONS

Chemical Abstracts 69:27279j (1968).
Chemical Abstracts 74:21815n (1971).

*Primary Examiner*—Jerome D. Goldberg
*Attorney, Agent, or Firm*—Gerald D. Sharkin; Robert S. Honor; Thomas O. McGovern

[57] ABSTRACT

6-(1-Piperazinyl)morphanthridine is a useful sleep promoting agent.

10 Claims, No Drawings

6-(1-PIPERAZINYL)MORPHANTHRIDINE AS A SLEEP INDUCING OR PROLONGING AGENT

This is a continuation-in-part of U.S. Pat. application Ser. No. 653,971, filed Jan. 30, 1976, now abandoned.

The present invention relates to the compound 6-(1-piperazinyl)morphantridine. It has now been found that this compound is useful as an agent for promoting, prolonging and inducing sleep, without significantly diminishing the paradoxical sleep phase, as indicated in standard tests. For example, in one test according to the principles of H. Kleinlogel, G. Sholtysik, and A. C. Sayers, Eur. J. Pharmacol. 33, (1975) 159–163, a decrease in the wake phase and an increase in the sleep phase in rats was observed for about eight hours after a single peroral administration of from about 1 to about 40 mg/kg animal body weight. In particular the effect on slow wave sleep was found to fade away after 3 hours and induce a consistent slight increase on paradoxical sleep over 8 hours. Moreover the compound does not induce undesirable extrapyramidal neuroleptic side effects, neurological side effects or circulatory side effects at sleep promoting, prolonging or inducing dosages, as indicated by standard tests in animals.

For the above-mentioned use the dosage will, of course, vary depending on the mode of administration and therapy desired. However, in general, satisfactory results are obtained when administered at a daily dosage of from about 0.01, preferably 0.1, to about 60 mg per kg animal body weight, conveniently given in a single dose shortly, e.g. 30 minutes, before retiring to sleep. For the larger mammal, the total daily dosage is preferably chosen to produce a duration of action lasting from about ½ hour to about 4 hours and is in the range from about 1 to 100 mg, preferably from about 1 to about 20 mg, especially 2 to 10 mg.

The compound may be administered orally in the form of tablets, powders, granules, capsules, suspensions, sirups and elixirs, or parenterally in the form of injectable solutions or suspensions. Oral administration is preferred. Aside from 6-(1-piperazinyl)morphantridine, the preparations may contain pharmaceutically inert organic or inorganic adjuvants, optionally granulating agents, binding agents, lubricants, dispersing agents, wetting agents and preservatives. Moreover, the pharmaceutical preparations may contain colouring, flavouring and sweetening substances, etc. Adjuvants for the production of tablets may be calcium carbonate, lactose, microcrystalline cellulose, mannitol or talc. Starch and alginic acid or microcrystalline cellulose may be used as granulating and disintegrating agents, starch, polyvinylpyrrolidone and gelatine may be used as binding agents, and magnesium stearate, stearic acid and talc as lubricants. Tablet formulations may be coated but are preferably uncoated. Suitable suspending agents for the production of liquid administration forms are especially methyl cellulose, tragacanth and sodium alginate. Suitable wetting agents are e.g. polyoxyethylene stearate and polyoxyethylene sorbitan-monooleate. Furthermore, preservatives such as p-hydroxy-benzoic acid alkyl ester may be used. Capsule formulations may contain 6-(1-piperazinyl)morphantridine on its own or together with an inert solid diluent, for example calcium phosphate, starch, lactose, mannitol and microcrystalline cellulose.

Solid preparations are preferred, especially hard-filled capsules and tablets, for reasons of easier production and favourable administration.

Preferably an unit dosage form is employed. Conveniently each unit dosage form contains a sufficient amount of 6-(1-piperazinyl)morphantridine such that two or only one unit dosage form need be administered a night. When a tablet formulation is used this may be formulated and shaped such that a half-tablet may be easily obtained and administered.

The 6-(1-piperazinyl)morphantridine is conveniently administered in salt form, e.g. the hydrochloride, malate, fumarate, methanesulphonate, benzenesulphonate, but preferably the maleate, (M.Pt. 176° – 178° C).

An example of a tablet formulation is as follows:

| | | |
|---|---|---|
| 6-(1-piperazinyl)-morphanthridine maleate | 3.5475 | mg (= 2,5 mg base) |
| mannitol | 46.9525 | mg |
| gelatine | 1.0 | mg |
| corn starch | 7.0 | mg |
| talc | 1.2 | mg |
| magnesium stearate | 0.3 | mg |
| | 60.0 | mg |

An example of a capsule formulation is as follows:

| | | |
|---|---|---|
| 6-(1-piperazinyl)-morphanthridine maleate | 3.5475 | mg (= 2.5 mg base) |
| Mannitol | 62.4525 | mg |
| Corn starch | 50.0 | mg |
| Talc | 2.0 | mg |
| Magnesium stearate | 2.0 | mg |
| | 120.0 | mg |

An example of an injectable solution is as follows:

| | | |
|---|---|---|
| 6-(1-piperazinyl)-morphanthridine | 2.5 | mg |
| Hydrochloric acid | 0.18 | ml |
| Propylene glycol | 1500.0 | mg |
| Dist. water to | 5.0 | ml |
| Buffer to pH 5-6 | | |
| Elixir | | |
| 6-(1-piperazinyl)-morphanthridine | 0.025 | g |
| Propylene glycol | 10.0 | g |
| Tinctura Aurantii dulcis | 10.0 | g |
| Saccharin | 0.02 | g |
| Karion F | 60.0 | g |
| Caramel-Sugar colouring | 0.05 | g |
| Ethyl alcohol pharm. | 15.0 | g |
| Citric acid | q.s. | |
| Dist. water to | 100.0 | ml |
| Buffer to pH 7 | | |

I clam:

1. A method for inducing, or prolonging sleep in animals, which comprises administering a sleep inducing, or prolonging effective amount of the compound 6-(1-piperazinyl)morphantridine to an animal in need of such treatment.

2. A method according to claim 1, wherein the compound is used to prolong sleep in an animal in need of such treatment.

3. The method of claim 1, wherein the compound is administered at a total daily dosage of from about 0.01 to about 60 mg/kg animal body weight of the compound.

4. The method of claim 1, wherein the compound is administered at a total daily dosage of from about 0.1 to about 60 mg/kg animal body weight of the compound.

5. The method of claim 3, wherein the compound is administered at a total daily dosage of from about 1 to about 20 mg.

6. The method of claim 3, wherein the compound is administered at a total daily dosage of from about 1 to about 10 mg.

7. The method of claim 3, wherein the compound is administered in unit dosage form before retiring to sleep.

8. The method of claim 7, wherein the compound is administered in a single dose 30 minutes before retiring to sleep.

9. The method of claim 8, wherein the compound is administered in the form of the maleate salt.

10. The method of claim 1 wherein the compound is administered at a total daily dosage of from about 2 to 10 mg.

* * * * *